(12) United States Patent
Tellier et al.

(10) Patent No.: US 11,596,929 B2
(45) Date of Patent: *Mar. 7, 2023

(54) FISCHER-TROPSCH PROCESS IN THE PRESENCE OF A CATALYST PREPARED FROM A MOLTEN SALT

(71) Applicant: IFP Energies nouvelles, Rueil-Malmaison (FR)

(72) Inventors: Elodie Tellier, Rueil-Malmaison (FR); Antoine Fecant, Rueil-Malmaison (FR); Eugenie Tavernier, Rueil-Malmaison (FR)

(73) Assignee: IFP Energies nouvelles, Rueil-Malmaison (FR)

(*) Notice: Subject to any disclaimer, the term of this patent is extended or adjusted under 35 U.S.C. 154(b) by 0 days.

This patent is subject to a terminal disclaimer.

(21) Appl. No.: 16/560,488

(22) Filed: Sep. 4, 2019

(65) Prior Publication Data
US 2020/0070129 A1 Mar. 5, 2020

(30) Foreign Application Priority Data

Sep. 4, 2018 (FR) ..................... 18/57.939

(51) Int. Cl.
| | |
|---|---|
| *C10G 2/00* | (2006.01) |
| *B01J 23/75* | (2006.01) |
| *B01J 21/12* | (2006.01) |
| *B01J 23/00* | (2006.01) |
| *B01J 35/02* | (2006.01) |
| *B01J 35/10* | (2006.01) |
| *B01J 37/02* | (2006.01) |
| *B01J 37/08* | (2006.01) |
| *C07C 1/04* | (2006.01) |

(52) U.S. Cl.
CPC .............. *B01J 23/75* (2013.01); *B01J 21/12* (2013.01); *B01J 23/005* (2013.01); *B01J 35/023* (2013.01); *B01J 35/1014* (2013.01); *B01J 35/1019* (2013.01); *B01J 35/1038* (2013.01); *B01J 35/1042* (2013.01); *B01J 35/1047* (2013.01); *B01J 37/0201* (2013.01); *B01J 37/08* (2013.01); *C07C 1/0435* (2013.01); *C10G 2/332* (2013.01); *C07C 2521/04* (2013.01); *C07C 2521/08* (2013.01); *C07C 2521/12* (2013.01); *C07C 2523/75* (2013.01); *C10G 2300/70* (2013.01)

(58) Field of Classification Search
None
See application file for complete search history.

(56) References Cited

U.S. PATENT DOCUMENTS

| | | | |
|---|---|---|---|
| 5,036,032 A | 7/1991 | Iglesia et al. | |
| 8,071,655 B2 * | 12/2011 | Diehl | ............... B01J 29/7088 518/715 |
| 2001/0051588 A1 | 12/2001 | Herron et al. | |
| 2015/0266006 A1 * | 9/2015 | Decottignies | ............ B01J 21/12 518/715 |
| 2017/0304807 A1 * | 10/2017 | Decottignies | .......... B01J 23/755 |

FOREIGN PATENT DOCUMENTS

WO    WO-2008090105 A2 *  7/2008  .......... B01J 23/8892

OTHER PUBLICATIONS

Search report in FR1857939 dated Apr. 4, 2019 (Year: 2019).*

* cited by examiner

*Primary Examiner* — Medhanit W Bahta
(74) *Attorney, Agent, or Firm* — Millen White Zelano & Branigan, PC; Brion P. Heaney

(57) ABSTRACT

Fischer-Tropsch process for the synthesis of hydrocarbons by bringing a feedstock including synthesis gas into contact with a catalyst prepared by the following:
- a porous support is brought into contact with a cobalt metal salt of which the melting point of the cobalt metal salt is between 30 and 150° C. for between 5 minutes and 5 hours, in order to form a solid mixture, the weight ratio of said cobalt metal salt to the porous oxide support being between 0.1 and 1;
- the solid mixture obtained is heated with stirring under atmospheric pressure at a temperature between the melting point of the cobalt metal salt and 200° C. for a period of time of between 30 minutes and 12 hours;
- the solid obtained is calcined at a temperature above 200° C. and below or equal to 1100° C.

12 Claims, No Drawings

FISCHER-TROPSCH PROCESS IN THE PRESENCE OF A CATALYST PREPARED FROM A MOLTEN SALT

TECHNICAL FIELD

The present invention relates to the field of reactions for the synthesis of hydrocarbons from a gas mixture comprising carbon monoxide and hydrogen, generally known as Fischer-Tropsch synthesis. The present invention also relates to the field of catalyst preparations used in Fischer-Tropsch syntheses.

STATE OF THE ART

Fischer-Tropsch synthesis processes make it possible to obtain a wide range of hydrocarbon cuts from the $CO+H_2$ mixture, commonly referred to as synthesis gas. The overall equation of Fischer-Tropsch synthesis can be written in the following way:

$$nCO+(2n+1)H_2 \rightarrow C_nH_{2n+2}+nH_2O$$

Fischer-Tropsch synthesis is at the core of processes for converting natural gas, coal or biomass into fuels or into intermediates for the chemical industry. These processes are referred to as GTL ("Gas to Liquids") in the case of the use of natural gas as initial feedstock, CTL ("Coal to Liquids") for coal, and BTL ("Biomass to Liquids") for biomass.

In each of these cases, the initial feedstock is first of all gasified into a synthesis gas which comprises a mixture of carbon monoxide and dihydrogen. The synthesis gas is subsequently converted mainly into paraffins by virtue of the Fischer-Tropsch synthesis, and these paraffins can subsequently be converted into fuels by a hydroisomerization-hydrocracking process. For example, conversion processes such as hydrocracking, deparaffinizing and hydroisomerization of heavy (C16+) cuts make it possible to produce various types of fuels in the middle-distillate range: gas oil (180-370° C. cut) and kerosene (140-300° C. cut). The lighter, C5-C15, fractions can be distilled and used as solvents.

The Fischer-Tropsch synthesis reaction can be carried out in various types of reactors (fixed-bed, mobile, or three-phase (gas, liquid, solid) for example of perfectly stirred autoclave or slurry bubble column type), and the reaction products have in particular the characteristic of being free of sulfur-comprising, nitrogenous or aromatic-type compounds.

In one embodiment in a reactor of slurry bubble column type (or else "slurry" type in a simplified expression), which uses a divided catalyst in the form of very fine power, typically about a few tens of micrometres, this powder forming a suspension with the reaction medium.

The Fischer-Tropsch reaction is carried out conventionally between 1 and 4 MPa (10 and 40 bar), at temperatures conventionally of between 200° C. and 350° C. The reaction is globally exothermic, which requires particular attention to the use of the catalyst.

The catalysts used for Fischer-Tropsch synthesis are essentially cobalt-based or iron-based catalysts, even though other metals can be used. Nevertheless, cobalt and iron offer a good performance/price compromise compared with other metals.

Conventional methods for preparing supported metal catalysts used for Fischer-Tropsch synthesis consist in depositing a metal salt dissolved in an aqueous solution on a porous support, then in carrying out one or more heat treatment(s) carried out under air, followed by a reducing treatment performed ex-situ or in-situ.

Moreover, other methods for Fischer-Tropsch catalyst synthesis are known from the prior art in order to improve the reducability of the metallic phase or else for controlling the particle sizes. Among these methods, the use of such molten salts as precursors is known from the literature.

Thus, it is known from patent U.S. Pat. No. 5,036,032 to propose a method for preparing a cobalt-based supported catalyst by rapid contacting (for a few tens of seconds) of a support in a cobalt nitrate molten salt bath, followed by a step of drying and reducing without intermediate calcining. This method enables the preferential localization of the cobalt phase at the periphery of the support. However, the method does not allow a precise control of the amount of cobalt deposited due to the very short contact time and furthermore the type of catalyst obtained is not suitable for use of the catalyst of slurry type owing to the excessive loss of metal by attrition. Moreover, the absence of a calcining step is risky since the reaction between the reducing element and the nitrates present in the solid is highly exothermic. Finally, this method makes it necessary to handle large amounts of (toxic) cobalt nitrate in liquid form and at temperature, with ratios of around 4 grams of cobalt precursor to 1 gram of support.

Finally, it is known from the publication in Chem Nano Mat., 2017, 3, p. 233-237, and in the Journal of the American Chemical Society, 2010, 132, p. 18318-18325, to prepare cobalt-based catalysts supported on mesoporous or meso-structured silica by static contacting of a molten cobalt nitrate hexahydrate salt and of a support, in a reactor of autoclave type under autogenic pressure and temperature for 12 hours to 8 days However, this method requires restrictive implementation through the use of a closed reactor (batch reactor), and also a synthesis time that is extremely long and thus detrimental on an industrial scale.

SUBJECTS OF THE INVENTION

The applicant has discovered, surprisingly, that it is possible to improve the catalytic performances in a Fischer-Tropsch process, and more particularly to significantly increase the activity of said catalyst by using a catalyst prepared according to one particular preparation mode having a reduced number of steps compared with the processes known from the prior art. The process for preparing such a catalyst allows an optimized control of the amount of metal deposited on the catalyst support, a simplification of the catalyst preparation steps, and also a decrease in the dangerousness and a controlled cost of the preparation process.

A subject of the present invention is a Fischer-Tropsch process for the synthesis of hydrocarbons, which comprises bringing a feedstock comprising a synthesis gas into contact with at least one catalyst under a total pressure between 0.1 and 15 MPa, at a temperature of between 150 and 350° C., and at an hour space velocity of between 100 and 20 000 volumes of synthesis gas per volume of catalyst and per hour with an $H_2/CO$ molar ratio of the synthesis gas between 0.5 and 4, said catalyst containing an active phase comprising at least cobalt and a porous support of oxide type, said catalyst being prepared by at least the following steps:

a) said porous oxide-type support is brought into contact with a cobalt metal salt of which the melting point of said cobalt metal salt is between 30 and 150° C., in order to form a solid mixture, the weight ratio of said cobalt metal salt to said porous oxide support being between 0.1 and 1;

b) the solid mixture obtained at the end of step a) is heated with stirring under atmospheric pressure at a temperature between the melting point of said cobalt metal salt and 200° C. for a period of time of between 5 minutes and 12 hours;

c) optionally, the solid obtained at the end of step b) is dried at a temperature below 200° C.;

d) the solid obtained at the end of step b) or c) is calcined at a temperature above 200° C. and below or equal to 1100° C. under an inert atmosphere or under an oxygen-containing atmosphere.

Preferably, said cobalt metal salt is chosen from cobalt nitrate hexahydrate or cobalt acetate tetrahydrate.

Preferably, the weight ratio of the cobalt metal salt to the porous support is between 0.3 and 0.9.

Preferably, step a) is carried out for 10 minutes to 4 hours.

Preferably, step b) is carried out for 30 minutes to 4 hours.

Preferably, the porous support of said catalyst is chosen from alumina, silica or silica-alumina.

In one embodiment according to the invention in which the porous support is a silica-alumina, the silica content is between 0.5% and 30% by weight relative to the weight of the porous support.

In one embodiment according to the invention, the porous support of said catalyst also comprises a phase of mixed oxide containing cobalt and/or nickel.

Advantageously, the content of mixed oxide phase in the porous support is between 0.1% and 50% by weight relative to the weight of the porous support.

Preferably, said porous support is in the form of a powder having a particle size of between 10 and 500 μm.

Preferably, said porous support comprises a specific surface area of between 50 and 500 $m^2/g$.

Preferably, said porous support has a total pore volume of between 0.3 and 1.2 ml/g.

Preferably, said porous support also comprises a simple oxide chosen from titanium oxide, ceria and zirconia, alone or as a mixture.

Preferably, the calcining time of step d) is at most 16 hours.

DETAILED DESCRIPTION OF THE INVENTION

Definitions

In the following description, the groups of chemical elements are given according to the CAS classification (CRC Handbook of Chemistry and Physics, published by CRC Press, Editor in Chief D. R. Lide, 81st edition, 2000-2001). For example, group VIIIB according to the CAS classification corresponds to the metals from columns 8, 9 and 10 according to the new IUPAC classification.

Textural and structural properties of the support and of the catalyst described below are determined by the characterization methods known to those skilled in the art. The total pore volume and the pore distribution are determined in the present invention by mercury porosimetry (cf. Rouquerol F.; Rouquerol J.; Singh K. "Adsorption by Powders & Porous Solids: Principle, methodology and applications", Academic Press, 1999). More particularly, the total pore volume is measured by mercury porosimetry according to the standard ASTM D4284-92 with a wetting angle of 140°, for example by means of an AutoporeIII™ model device from the brand Micromeritics™. The specific surface area is determined in the present invention by the B.E.T. method, which method is described in the same reference book as the mercury porosimetry, and more particularly according to the standard ASTM D3663-03.

Fischer-Tropsch Process

The Fischer-Tropsch process according to the invention leads to the production of essentially linear and saturated $C_5^+$ hydrocarbons (having at least 5 carbon atoms per molecule). The hydrocarbons produced by the process of the invention are thus essentially paraffinic hydrocarbons, the fraction of which having the highest boiling points can be converted with a high yield to middle distillates (gas oil and kerosene cuts) by a hydroconversion process such as catalytic hydrocracking and/or hydroisomerization.

The feedstock used for the implementation of the process of the invention comprises synthesis gas. Synthesis gas is a mixture comprising in particular carbon monoxide and hydrogen having $H_2/CO$ molar ratios that may vary in a ratio of 0.5 to 4 depending on the process by which it was obtained. The $H_2/CO$ molar ratio of the synthesis gas is generally close to 3 when the synthesis gas is obtained from the hydrocarbon or alcohol steam reforming process. The $H_2/CO$ molar ratio of the synthesis gas is of the order of 1.5 to 2 when the synthesis gas is obtained from a partial oxidation process. The $H_2/CO$ molar ratio of the synthesis gas is generally close to 2.5 when it is obtained from a thermal reforming process. The $H_2/CO$ molar ratio of the synthesis gas is generally close to 1 when it is obtained from a process for gasification and reforming of $CO_2$.

The catalyst used in the hydrocarbon synthesis process according to the invention is preferably carried out in ebullated-bed or else three-phase fluidized-bed reactors. The implementation of the catalyst suspended in a three-phase fluidized reactor, preferentially of bubble column type, is preferred. In this preferred use of the catalyst, said catalyst forms a suspension with the reaction medium. This technology is also known under the "slurry" process terminology by those skilled in the art.

The hydrocarbon synthesis process according to the invention is performed under a total pressure of between 0.1 and 15 MPa, preferably between 0.5 and 10 MPa, under a temperature of between 150 and 350° C., preferably between 180 and 270° C. The hourly space velocity is advantageously between 100 and 20 000 volumes of synthesis gas per volume of catalyst and per hour (100 to 20 000 $h^{-1}$) and preferably between 400 and 10 000 volumes of synthesis gas per volume of catalyst and per hour (400 to 10 000 $h^{-1}$).

Catalyst Preparation Process

The cobalt-based supported catalyst used in the Fischer-Tropsch synthesis is prepared by a preparation process comprising at least the following steps:

a) a porous oxide-type support is brought into contact with a cobalt metal salt of which the melting point of said metal salt is between 30 and 150° C., in order to form a solid mixture, the weight ratio of said cobalt metal salt to said porous oxide support being between 0.1 and 1;

b) the solid mixture obtained at the end of step a) is heated with stirring under atmospheric pressure at a temperature between the melting point of said cobalt metal salt and 200° C. for a period of time of between 5 minutes and 12 hours;

c) optionally, the solid obtained at the end of step b) is dried at a temperature below 200° C.;

d) the solid obtained at the end of step b) or c) is calcined at a temperature of between 200 and 1100° C. under an inert atmosphere or under an oxygen-containing atmosphere.

The steps of the process for preparing the catalyst used in the Fischer-Tropsch synthesis according to the invention are described in detail below.

Step a)

According to step a), a porous oxide-type support is brought into contact with a cobalt metal salt of which the melting point of said metal salt is between 30 and 150° C., in order to form a solid mixture, the weight ratio of said cobalt metal salt to said porous oxide support being between 0.1 and 1.

Preferably, the porous support comprises alumina, silica or a silica-alumina. When the support is a silica-alumina, the silica ($SiO_2$) content can range from 0.5% by weight to 30% by weight relative to the weight of the support, preferably between 0.6% and 15% by weight. According to one variant, said porous support also contains a phase of mixed oxide containing cobalt and/or nickel. According to this variant, the content of the mixed oxide phase in the support is between 0.1% and 50% by weight relative to the weight of the support.

Preferably, the mixed oxide phase comprises an aluminate of formula $CoAl_2O_4$ or $NiAl_2O_4$ in the case of an alumina-based or silica-alumina-based support, or a silicate of formula $Co_2SiO_4$ or $Ni_2SiO_4$ in the case of a silica-based or silica-alumina-based support. A phase of mixed oxide containing cobalt and/or nickel is understood to mean a phase in which cations of cobalt and/or of nickel are combined with the $O^{2-}$ oxide ions of the alumina and/or silica support thus forming a mixed phase containing the aluminates and/or silicates containing cobalt and/or nickel.

The mixed oxide phase may be in amorphous form or in crystalline form. When the support is based on alumina, the mixed oxide phase may comprise an aluminate of formula $CoAl_2O_4$ or $NiAl_2O_4$, in amorphous or crystalline form, for example in spinel form. When the support is based on silica, the mixed oxide phase may comprise a silicate of formula $Co_2SiO_4$ or $Ni_2SiO_4$ (cobalt orthosilicate or nickel orthosilicate), in amorphous or crystalline form. When the support is based on silica-alumina, the mixed oxide phase may comprise an aluminate of formula $CoAl_2O_4$ or $NiAl_2O_4$ in amorphous or crystalline form, for example in spinel form, and/or a silicate of formula $Co_2SiO_4$ or $Ni_2SiO_4$, in amorphous or crystalline form.

The cobalt and/or nickel contained in the mixed oxide phase cannot be reduced during the final activation of the Fischer-Tropsch (reduction) catalyst. The cobalt and/or nickel contained in the mixed oxide phase does not therefore constitute the active phase of the catalyst.

The presence of a mixed oxide phase in the catalyst according to the invention is measured by temperature-programmed reduction (or TPR) such as for example described in Oil & Gas Science and Technology, Rev. IFP, Vol. 64 (2009), No. 1, pp. 11-12. According to this technique, the catalyst is heated in a stream of a reducing agent, for example in a stream of dihydrogen. The measurement of the dihydrogen consumed as a function of the temperature gives quantitative information regarding the reducibility of the species present. The presence of a mixed oxide phase in the catalyst is thus expressed by a consumption of dihydrogen at a temperature above around 800° C.

The support comprising alumina, silica or a silica-alumina, optionally comprising at least one mixed oxide phase as described above, may also comprise a simple oxide chosen from titanium oxide ($TiO_2$), ceria ($CeO_2$) and zirconia ($ZrO_2$), alone or as a mixture.

The specific surface area of the support is generally between 50 $m^2/g$ and 500 $m^2/g$, preferably between 100 $m^2/g$ and 300 $m^2/g$, more preferably between 150 $m^2/g$ and 250 $m^2/g$.

The pore volume of said support is generally between 0.3 ml/g and 1.2 ml/g, and preferably between 0.4 ml/g and 1 ml/g.

The pore distribution of the pores of the porous support may be of monomodal, bimodal or plurimodal type Preferably, it is of monomodal type. The pore size is about from 2 to 50 nm, with an average pore size between 5 and 25 nm, preferably between 8 and 20 nm.

The support may have a morphology in the form of beads, extrudates (for example of trilobe or quadrilobe shape) or pellets, especially when said catalyst is used in a reactor operating as a fixed bed, or may have a morphology in the form of a powder of variable particle size, especially when said catalyst is used in a slurry bubble column. Preferably, the support is in the form of a powder having a particle size of between 10 and 500 μm.

The support can be provided by any means known to those skilled in the art.

According to step a), a solid cobalt metal salt is provided such that its melting point is between 30° C. and 150° C. In step a), the metal salt is in solid form, i.e. said porous support and said metal salt are brought into contact at a temperature below the melting point of said metal salt. Preferably, the cobalt metal salt is hydrated. Preferably, the cobalt metal salt is cobalt nitrate hexahydrate or cobalt acetate tetrahydrate. Very preferably, the cobalt metal salt is cobalt nitrate hexahydrate. The metal salt according to the invention is preferably in the form of a powder with a variable particle size and/or of particles of millimetric size.

The weight ratio of the cobalt metal salt to the porous support is between 0.1 and 1, preferably between 0.3 and 0.9. The preparation process allows optimized control of the amount of metal deposited on the catalyst, and also a dangerousness and a cost controlled by the minimization of the amount of metal precursor used not exceeding 1 gram of metal precursor per gram of support.

According to step a), said porous oxide support and the cobalt metal salt may be brought into contact by any method known to those skilled in the art. Preferably, said porous support and the cobalt metal salt are brought into contact with contacting means chosen from convective mixers, drum mixers or static mixers. Step a) is carried out for a period of between 5 minutes and 5 hours depending on the type of mixer used, preferably between 10 minutes and 4 hours, and more preferentially still between 15 minutes and 3 hours.

According to one variant of step a), any other organic or inorganic solid compound in the form of powder with a variable particle size may be added to the mixture. If it is an inorganic compound, it may contain at least one element chosen from groups VIIB, VIII, IB, IIB, IA (alkali metal element), IIA (alkaline-earth metal element) and IIIA, alone or as a mixture. When another organic or inorganic compound is added to the mixture, the weight ratio of the cobalt metal precursor and said compound is between 10 and 50 000, preferably between 50 and 20 000.

Step b)

According to step b), the mixture obtained at the end of step a) is heated with stirring at atmospheric pressure at a temperature between the melting point of the cobalt metal salt and 200° C. In the very preferred case where the cobalt metal salt is cobalt nitrate hexahydrate, the temperature is between 55 and 150° C., preferably between 65 and 130° C.

The residence time is between 5 minutes and 12 hours, preferably between 5 minutes and 4 hours.

During step b), the mechanical homogenization of the mixture may be carried out by any method known to those skilled in the art. Preferably, use will be made of convective mixers, drum mixers or static mixers.

Step c) (Optional Step)

According to the optional step c), the drying of the solid obtained in step b) is carried out at a temperature below 200° C., advantageously between 50° C. and 180° C., preferably between 70° C. and 150° C., very preferably between 75° C. and 130° C.

The drying step is preferentially carried out for a maximum period of 4 hours, preferably under an inert atmosphere or under an oxygen-containing atmosphere.

The optional drying step may be carried out by any technique known to those skilled in the art. It is advantageously carried out at atmospheric pressure or at reduced pressure. Preferably, this step is carried out at atmospheric pressure. It is advantageously carried out using hot air or any other hot gas. Preferably, the gas used is either air, or an inert gas such as argon or nitrogen. Very preferably, the drying is carried out in the presence of nitrogen and/or air. Unlike step b), the drying step c) is not carried out with stirring by any means whatsoever.

Step d)

According to step d), the solid obtained in step b) or c) undergoes a calcination treatment at a temperature above 200° C. and below or equal to 1100° C., preferably at a temperature between 250 and 600° C., under an inert atmosphere (nitrogen for example) or under an oxygen-containing atmosphere (air for example). The duration of this heat treatment is generally less than 16 hours, preferably less than 5 hours. After this treatment, the cobalt is in oxide form and the solid no longer contains any or contains very little of the anion initially present in the precursor metal cobalt salt. The calcining step may be carried out by any technique known to those skilled in the art. It is advantageously carried out in a crossed bed or in a fluidized bed using hot air or any other hot gas.

Prior to its used in the Fischer-Tropsch synthesis catalytic reactor, the catalyst obtained at the end of step d) generally undergoes a reducing treatment, for example under pure or diluted hydrogen, at high temperature, intended to activate the catalyst and to form particles of metal in the zero-valent state (in metal form). This treatment is carried out in-situ (in the same reactor as the one where the Fischer-Tropsch synthesis is carried out) or ex-situ before being loaded into the reactor. The temperature of this reducing treatment is preferentially between 200 and 500° C. and the duration thereof is generally between 2 and 20 hours.

Catalyst

The catalyst obtained by means of the preparation process described above comprises an active phase comprising at least cobalt and a porous support of oxides. The content of cobalt element represents from 1% to 60% by weight, preferably from 5% to 30% by weight and very preferably from 10% to 30% by weight, relative to the weight of the catalyst.

The specific surface area of the catalyst containing the active phase and the oxides support is generally between 50 $m^2/g$ and 500 $m^2/g$, preferably between 80 $m^2/g$ and 250 $m^2/g$, more preferably between 90 $m^2/g$ and 150 $m^2/g$. The pore volume of said catalyst is generally between 0.2 ml/g and 1 ml/g, and preferably between 0.25 ml/g and 0.8 ml/g.

Preferably, the pore distribution of the catalyst is monomodal.

In order to illustrate the invention and to allow those skilled in the art to carry it out, various embodiments of the process for preparing cobalt-based supported catalysts and the use thereof in Fischer-Tropsch synthesis are presented below; however, this could not limit the scope of the invention.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 18/57.939, filed Sep. 4, 2018, are incorporated by reference herein.

EXAMPLES

Example 1 (Comparative): Catalyst A of Formula Co/$Al_2O_3 \cdot SiO_2$—Deposition by Dry Impregnation A catalyst A comprising cobalt deposited on a silica-alumina ($Al_2O_3 \cdot SiO_2$) support is prepared by dry impregnation of an aqueous solution of cobalt nitrate (Orrion Chemicals Metalchem, ~13% by weight Co) so as to deposit, in two steps, approximately 15% by weight of Co on a silica-alumina initially containing 5% by weight of $SiO_2$, having an average particle size equal to 80 µm, and having a specific surface area of 180 $m^2/g$ and a pore volume of 0.55 ml/g After a first dry impregnation with a solution of cobalt nitrate at maximum concentration (~13% by weight), the solid is dried in a crossed bed at 120° C. for 3 h under air, then calcined at 400° C. for 4 h in a crossed bed. The preceding steps are repeated a second time. The final catalyst A which contains 14.7% by weight of Co (in $Co_3O_4$ oxide form) relative to the weight of the catalyst is obtained.

Example 2 (Comparative): Catalyst B of Formula Co/$CoAl_2O_4$—$Al_2O_3 \cdot SiO_2$—Deposition by Dry Impregnation A catalyst B comprising cobalt deposited on a support, based on a mixed oxide phase (in spinel form) included in a silica-alumina, is prepared by dry impregnation of an aqueous solution of cobalt nitrate (Orrion Chemicals Metalchem, ~13% by weight Co) so as to deposit, in two steps, around 15% by weight of cobalt on the support.

The spinel present in the support of the catalyst B is a simple spinel formed of cobalt aluminate, which is included in a silica-alumina containing 5% by weight of $SiO_2$, having an average particle size equal to 80 µm and having a specific surface area of 180 $m^2/g$ and a pore volume of 0.55 ml/g. The preparation of the spinel included in the silica-alumina is carried out by dry impregnation of an aqueous solution of cobalt nitrate (Orrion Chemicals Metalchem, ~13% by weight Co) so as to introduce 4% by weight of Co into said silica-alumina. After drying at 120° C. for 3 hours, the solid is calcined at 850° C. for 4 hours under air. The support for the catalyst denoted by B' is formed of 4% by weight of cobalt in the form of cobalt aluminate (i.e. 12% by weight of spinel) in the silica-alumina.

The cobalt-based active phase is then deposited on said support B' in two steps, by dry impregnation, according to a protocol that is identical to that described for the preparation of the catalyst A. The drying and calcining steps are also performed under the same operating conditions as those of example 1. The concentration of cobalt in the solution of cobalt nitrate, used for the successive impregnations, is at the maximum in order to obtain the catalyst B with the desired final Co content.

The final catalyst B has a total cobalt content of 19.6% by weight (the content of Co present in the spinel phase being included) relative to the weight of the catalyst and a content of cobalt in $Co_3O_4$ oxide form of 15.6% by weight relative to the weight of the catalyst.

Example 3 (Comparative): Catalyst C of Formula $Co/Al_2O_3 \cdot SiO_2$—Deposition Using a Molten Salt in an Autoclave A catalyst C comprising cobalt deposited on a silica-alumina support is prepared by infiltration of molten cobalt nitrate salt so as to deposit, in one step, around 13% by weight of Co on a silica-alumina initially containing 5% by weight of $SiO_2$ having an average particle size equal to 80 µm and having a specific surface area of 180 m$^2$/g and a pore volume of 0.55 ml/g, by a method drawn from T. M. Eggenhuisen et al. J. Am. Chem. Soc., 2010, 132, p. 18318-18325. After a step of homogenization with a mortar, 5 g of silica-alumina support and 4 g of cobalt nitrate hexahydrate (Aldrich, >98%) are introduced into a closed autoclave statically heated at 60° C. for 24 h under autogenic pressure.

After the step of infiltration of molten salt in an autoclave, the solid obtained is dried in a crossed bed at 120° C. for 3 h under air and then calcined at 400° C. for 4 h in a crossed bed.

The final catalyst C which contains 13.2% by weight of Co (in $Co_3O_4$ oxide form) relative to the weight of the catalyst is obtained.

Example 4 (Comparative): Catalyst D of Formula $Co/Al_2O_3 \cdot SiO_2$—Short-Residence-Time Deposition Using a Cobalt Nitrate Salt in an Autoclave A catalyst D comprising cobalt deposited on a silica-alumina support is prepared by infiltration of cobalt nitrate salt so as to deposit cobalt, in one step, on a silica-alumina initially containing 5% by weight of $SiO_2$ having an average particle size equal to 80 µm and having a specific surface area of 180 m$^2$/g and a pore volume of 0.55 ml/g, by a method drawn from patent U.S. Pat. No. 5,036,032 in order for the contact time between the support and the cobalt salt during the deposition to be very short (<1 minute).

10 g of silica-alumina support are inserted into an assembly of vacuum filtration on a Millipore® filter having a porosity of 0.45 µm. In parallel, 20 g of cobalt nitrate hexahydrate (Aldrich, >98%) are placed in a beaker and heated to 80° C. After the drawing of the vacuum of the filtration assembly has been turned on, the molten salt at 80° C. is poured into the filtration assembly on the silica-alumina support. The approximate contact time between the silica-alumina support and the molten salt is around 10 seconds.

After the step of infiltration of molten salt, the solid obtained is recovered then dried in a crossed bed at 120° C. for 3 h under air and then calcined at 400° C. for 4 h in a crossed bed. The final catalyst D which contains 7.3% by weight of Co (in $Co_3O_4$ oxide form) relative to the weight of the catalyst is obtained.

Example 5 (According to the Invention): Catalyst E of Formula $Co/Al_2O_3 \cdot SiO_2$ A catalyst E comprising cobalt deposited on a silica-alumina support is prepared by infiltration of molten cobalt nitrate salt so as to deposit, in one step, around 13% by weight of Co on a silica-alumina initially containing 5% by weight of $SiO_2$ having an average particle size equal to 80 µm and having a specific surface area of 180 m$^2$/g and a pore volume of 0.55 ml/g.

5 g of silica-alumina support and 4 g of cobalt nitrate hexahydrate (Aldrich, >98%) are introduced into a drum mixer inclined at 45° and equipped with baffles to ensure a cascade movement during the mixing of the powders. The mixers are stirred at 60 rpm for 1 hour at ambient temperature and pressure. After this homogenization step, the mixer is left to stir at ambient pressure, and the temperature is increased at 5° C./min up to 80° C. and left for 1 hour.

The solid obtained is then calcined at 400° C. for 4 h in a crossed bed. The final catalyst E which contains 13.0% by weight of Co (in $Co_3O_4$ oxide form) relative to the weight of the catalyst is obtained.

Example 6 (According to the Invention): Catalyst F of Formula $Co/CoAl_2O_4$—$Al_2O_3.SiO_2$ A catalyst F comprising cobalt deposited on a support, based on a mixed oxide phase (in spinel form) included in a silica-alumina, is prepared by infiltration of molten cobalt nitrate salt so as to deposit, in one step, around 13% by weight of Co on the support.

The spinel present in the support of the catalyst F is a simple spinel formed of cobalt aluminate, which is included in a silica-alumina containing 5% by weight of $SiO_2$, having an average particle size equal to 80 µm and having a specific surface area of 180 m$^2$/g and a pore volume of 0.55 ml/g. The preparation of the spinel included in the silica-alumina is carried out by dry impregnation of an aqueous solution of cobalt nitrate (Orrion Chemicals Metalchem, ~13% by weight Co) so as to introduce 4% by weight of Co into said silica-alumina. After drying at 120° C. for 3 hours, the solid is calcined at 850° C. for 4 hours under air. The support for the catalyst denoted by F' is formed of 4% by weight of cobalt in the form of cobalt aluminate (i.e. 12% by weight of spinel) in the silica-alumina.

The cobalt-based active phase is then deposited on said support F' in one step, by infiltration of molten cobalt nitrate salt, according to a protocol identical to that described for the preparation of the catalyst E. The calcining step is also carried out under the same operating conditions as those of Example 5.

The final catalyst F has a total cobalt content of 17.1% by weight (the content of Co present in the spinel phase being included) and a content of cobalt in $Co_3O_4$ oxide form of 13.1% by weight relative to the weight of the catalyst.

Example 7: Use of the Catalysts A to F in Fischer-Tropsch Synthesis

The catalysts A to F, before being successively tested in conversion of the synthesis gas, are reduced ex-situ under a stream of pure hydrogen at 400° C. for 16 hours in a tubular reactor. Once the catalyst has been reduced, it is discharged under an argon atmosphere and coated in Sasolwax® to be stored with exclusion of air before testing. The Fischer-Tropsch synthesis reaction is carried out in a slurry-type reactor operating continuously and operating with a concentration of 10% (vol) of catalyst in slurry phase.

The test conditions are the following: temperature=230° C.; total pressure=2 MPa; $H_2$/CO molar ratio=2. The conversion of the CO is maintained between 45% and 50% throughout the duration of the test. The test conditions are adjusted so as to be at iso conversion of CO regardless of the activity of the catalyst.

The results, in terms of activity, were calculated for the catalysts A to E relative to the catalyst A serving as reference, and are shown in Table 1 below. The methane-formation selectivities are also given.

TABLE 1

Catalytic performances of the catalysts A to F

| Catalysts | Relative activity after 300 h of test under syngas feedstock | Methane formation selectivity (%) |
| --- | --- | --- |
| A (not in accordance) | 100 (base) | 12 |
| B (not in accordance) | 125 | 10 |
| C (not in accordance) | 121 | 12 |
| D (not in accordance) | 82 | 10 |
| E (in accordance) | 157 | 10 |
| F (in accordance) | 172 | 9 |

The results of Table 1 above show the catalytic performances of the catalysts A to F both in terms of activity and in terms of selectivity. It appears that the catalysts prepared by the process according to the invention are obtained in fewer unit steps, and exhibit in particular, at reduced final concentration of cobalt, performances that are better than the catalysts A to D that are not in accordance.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A Fischer-Tropsch process for the synthesis of hydrocarbons, wherein the process comprises:
    bringing a feedstock comprising a synthesis gas into contact with at least one catalyst under a total pressure between 0.1 and 15 MPa, at a temperature of between 150 and 350° C., and at an hour space velocity of between 100 and 20 000 volumes of synthesis gas per volume of catalyst and per hour with an $H_2$/CO molar ratio of the synthesis gas between 0.5 and 4,
    wherein said catalyst contains an active phase comprising a porous support consisting of Si, Al and O or Co, Si, Al and O selected from the groups consisting of $Al_2O_3 \cdot SiO_2$ and $CoAl_2O_4$—$Al_2O_3 \cdot SiO_2$ porous supports,
    wherein said catalyst is prepared by a preparation process consisting of:
    a) bringing said $Al_2O_3 \cdot SiO_2$ or $CoAl_2O_4$—$Al_2O_3 \cdot SiO_2$ porous support into contact with a cobalt metal salt, wherein the melting point of said cobalt metal salt is between 30 and 150° C., for a period of time of between 5 minutes and 5 hours, the weight ratio of said cobalt metal salt to said $Al_2O_3 \cdot SiO_2$ or $CoAl_2O_4$—$Al_2O_3 \cdot SiO_2$ porous support being between 0.1 and 1, and forming a solid mixture;
    b) heating the solid mixture obtained at the end of a) with stirring under atmospheric pressure at a temperature between the melting point of said cobalt metal salt and 200° C. for a period of time between 5 minutes and 12 hours; and
    c) obtaining a solid at the end of b) and calcining said solid at a temperature above 200° C. and below or equal to 1100° C. under an inert atmosphere or under an oxygen-containing atmosphere.

2. The process according to claim 1, wherein said cobalt metal salt is cobalt nitrate hexahydrate.

3. The process according to claim 1, wherein the weight ratio of the cobalt metal salt to the $Al_2O_3 \cdot SiO_2$ or $CoAl_2O_4$—$Al_2O_3 \cdot SiO_2$ porous support is between 0.3 and 0.9.

4. The process according to claim 1, wherein a) is carried out for 10 minutes to 4 hours.

5. The process according to claim 1, wherein b) is carried out for 5 minutes to 4 hours.

6. The process according to claim 1, wherein said $Al_2O_3 \cdot SiO_2$ or $CoAl_2O_4$—$Al_2O_3 \cdot SiO_2$ porous support is in the form of a powder having a particle size of between 10 and 500 μm.

7. The process according to claim 1, wherein said $Al_2O_3 \cdot SiO_2$ or $CoAl_2O_4$—$Al_2O_3 \cdot SiO_2$ porous support has a specific surface area of between 50 and 500 $m^2$/g.

8. The process according to claim 1, wherein said $Al_2O_3 \cdot SiO_2$ or $CoAl_2O_4$—$Al_2O_3 \cdot SiO_2$ porous support has a total pore volume of between 0.3 and 1.2 ml/g.

9. The process according to claim 1, wherein the calcining time of c) is at most 16 hours.

10. The process according to claim 1, wherein the active phase comprises an $Al_2O_3 \cdot SiO_2$ porous support.

11. The process according to claim 1, wherein the active phase comprises an $CoAl_2O_4$—$Al_2O_3 \cdot SiO_2$ porous support.

12. The process according to claim 1, wherein said cobalt metal salt is cobalt acetate tetrahydrate.

* * * * *